(12) United States Patent
Mahalingam et al.

(10) Patent No.: US 10,972,847 B2
(45) Date of Patent: Apr. 6, 2021

(54) CALIBRATION METHOD FOR HEARING PROTECTION DEVICES

(71) Applicant: HONEYWELL INTERNATIONAL INC., Morris Plains, NJ (US)

(72) Inventors: Muneeswaran Mahalingam, Hyderabad (IN); Mehabube Rabbanee Shaik, Hyderabad (IN); Srinivasa Rao Bommana, Hyderabad (IN)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 0 days.

(21) Appl. No.: 16/349,054

(22) PCT Filed: Nov. 10, 2016

(86) PCT No.: PCT/US2016/061269
§ 371 (c)(1),
(2) Date: May 10, 2019

(87) PCT Pub. No.: WO2018/089003
PCT Pub. Date: May 17, 2018

(65) Prior Publication Data
US 2019/0273998 A1 Sep. 5, 2019

(51) Int. Cl.
*H04R 29/00* (2006.01)
*A61F 11/14* (2006.01)
(Continued)

(52) U.S. Cl.
CPC ............ *H04R 29/001* (2013.01); *A61F 11/14* (2013.01); *H03F 3/181* (2013.01); *H03G 3/02* (2013.01);
(Continued)

(58) Field of Classification Search
CPC ...... H04R 29/004; H04R 25/70; H04R 29/00; H04R 25/30
(Continued)

(56) References Cited

U.S. PATENT DOCUMENTS 7,715,571 B2 * 5/2010 Boretzki ................ H04R 25/70
381/312
10,341,790 B2 * 7/2019 Shennib ............... H04R 25/554
(Continued)

OTHER PUBLICATIONS

International Search Report and Written Opinion for International Application No. PCT/US2016/061269, dated Jul. 7, 2017, 12 pages.
(Continued)

*Primary Examiner* — Alexander Krzystan
(74) *Attorney, Agent, or Firm* — Alston & Bird LLP

(57) ABSTRACT

Embodiments relate generally to hearing protection devices which incorporate a calibration mode which allows the user to perform a calibration test to determine an individualized hearing threshold. Embodiments of the device may also comprise a normal mode to prevent input signals greater than the individualized hearing threshold from being transmitted to the user's ear canal. In addition, embodiments may comprise a normal mode configured to limit input signals to less than or equal to a standard industry threshold in the case no calibration test has been completed by the user. This may increase user comfort and prevent hearing damage.

17 Claims, 5 Drawing Sheets

(51) Int. Cl.

| | |
|---|---|
| *H03F 3/181* | (2006.01) |
| *H03G 3/30* | (2006.01) |
| *H04R 1/10* | (2006.01) |
| *H04R 5/04* | (2006.01) |
| *H03G 3/02* | (2006.01) |
| *H04R 5/033* | (2006.01) |

(52) U.S. Cl.
CPC ........... *H03G 3/301* (2013.01); *H03G 3/3005* (2013.01); *H04R 1/1008* (2013.01); *H04R 1/1041* (2013.01); *H04R 1/1083* (2013.01); *H04R 1/1091* (2013.01); *H04R 5/04* (2013.01); *A61F 2011/145* (2013.01); *H03F 2200/03* (2013.01); *H03F 2200/129* (2013.01); *H03G 2201/103* (2013.01); *H04R 5/033* (2013.01); *H04R 2420/07* (2013.01); *H04R 2430/01* (2013.01)

(58) Field of Classification Search
USPC ............................................ 381/314, 60, 58
See application file for complete search history.

(56) References Cited

U.S. PATENT DOCUMENTS

| | | | |
|---|---|---|---|
| 2003/0198357 | A1 | 10/2003 | Schneider et al. |
| 2007/0223721 | A1 | 9/2007 | Stern et al. |
| 2011/0270014 | A1 | 11/2011 | Flynn et al. |
| 2012/0014553 | A1* | 1/2012 | Bonanno ................. G10L 15/00 381/364 |
| 2013/0102923 | A1 | 4/2013 | Cas et al. |
| 2017/0027522 | A1* | 2/2017 | Van Hasselt ........... A61B 5/123 |
| 2018/0034427 | A1* | 2/2018 | Mostert ................. H03F 3/2173 |
| 2018/0035207 | A1* | 2/2018 | Hsu ......................... H04W 4/80 |

OTHER PUBLICATIONS

Examination Report No. 1 for Australian Patent Application. No. 2016429412, dated Mar. 30, 2020, 4 pages.
Communication pursuant to Rules 161(1) and 162 for European Patent Application No. 16798363.4, dated Jun. 19, 2019, 3 pages.
Intention to Grant for European Patent Application No. 16798363.4 dated Jul. 3, 2020, 5 pages.
Notice of Acceptance issued in Australian Application No. 2016429412, dated Oct. 7, 2020, 3 pages.
Decision to grant a European patent dated Dec. 10, 2020 for EP Application No. 16798363.4, 2 pages.

* cited by examiner

CALIBRATION METHOD FOR HEARING PROTECTION DEVICES

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments generally relate to improved hearing protection and, more specifically, to hearing protection devices with speakers that serve to protect the user's hearing from damage or discomfort due to speaker volume by allowing the user to calibrate the device to his/her individual hearing threshold level.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
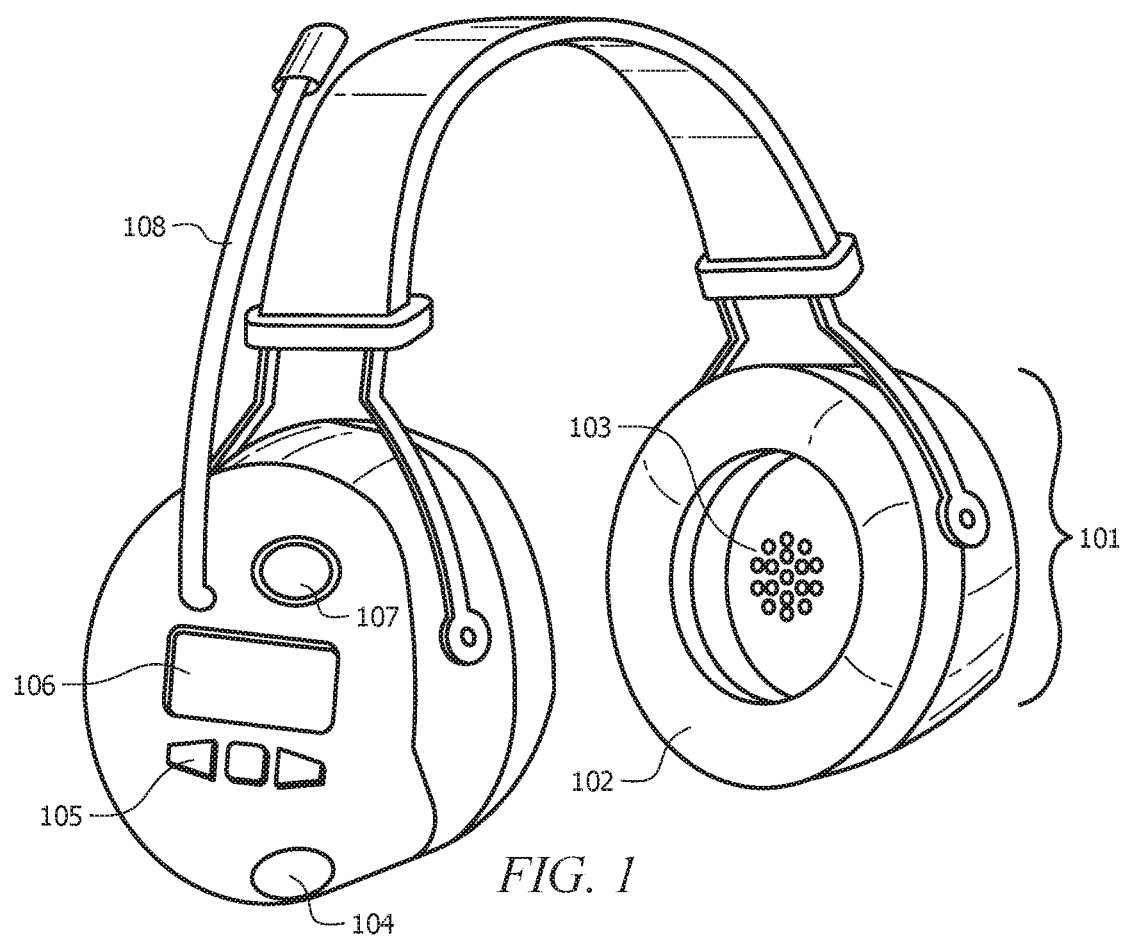
FIG. 1 illustrates a perspective view of an exemplary embodiment of an earmuff hearing protection device with external electronic elements.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The embodiments of this disclosure typically relate to improved hearing protection, and might, for example typically relate to hearing protection devices, such as earmuffs, having a speaker directed inward towards a user's ear. Typically, industry and/or regulations may have a standard sound level limitation for workers' noise exposure, for example over the course of a work shift. For example, a worker in an 8 hour work shift should not be exposed to sound over 82 A-weighted decibels (dBA) (e.g. based on The National Institute of Health and Safety (NIOSH) sound level limitation). Thus, if sound levels in the work environment are above that limit, the use of heating protection would be required. Additionally, if the hearing protection device has speakers (for example allowing sound to pass-through and/or radio communication and/or entertainment sound like music), then the speaker output should be limited to not exceed the sound level limitation in order to protect a user's ears from damage and/or discomfort. So, for example, speaker sound in a hearing protection device might be limited to 82 dBA as a standard threshold (or some other limit set by industry or regulation). However, 82 dBA may not be an accurate sound level limitation for every user and may lead to impairment of the user's long term hearing ability with regular usage and/or user discomfort. This may be because each user may have varying sound level sensitivity and efficiency as a result of each user having a unique shape and structure of the ear canal, thickness and area of the eardrum, and available number of sensing hairs. Additionally, users may have prior hearing impairment in one ear, resulting in different sound level limitations between the left ear and right ear. Thus, disclosed embodiments may allow the user to configure the sound level limitation for an exemplary hearing protection device based on his/her hearing preference (e.g. individualized threshold). This may be accomplished by the user interacting with the system to perform a calibration test. The calibration test may be performed for both ears at once (for example, both the left ear and right ear having the same sound level limitation) or the calibration test may be performed individually for each ear (for example, the left ear having a different sound level limitation than the right ear). The user may also choose not to perform a calibration test to determine his/her own hearing threshold, in which case the standard sound level limitation of 82 dBA may be the standard/default sound level threshold for both ears. Thus, embodiments of the present invention may address one or more such issues by allowing the user to configure the device to his/her own hearing threshold in an attempt to prevent hearing damage and increase user comfort.

Disclosed embodiments relate to improved heating protection, which might, for example, be used in hearing protection devices such as earmuffs. Alternatively, hearing protection devices might include ear tips, ear plugs, headphones, or any other speaker for the ear (which typically blocks at least some environmental/surrounding noise). Typically, disclosed embodiments would include a speaker, a processor, a user interface, an input signal source, and, optionally, a sealing element. For example, the sealing element may be configured to seal a user's ear canal and/or provide sound attenuation to protect the user's ears from potentially damaging external sounds and may function as a hearing protection device, such as an earmuff. The input signal source may come from an external microphone (for external sound pass-through) which might be mounted on the exterior of the hearing protection device, a wireless communication device (such as a built-in radio communicator or an external radio communicator transmitting to the speaker via a port or plug), or air entertainment device such as an iPod or mp3 player (which might be built-in or might be separate and input to the hearing protection device by a port or plug). The user interface may be located on the exterior of the hearing protection device and may comprise one or more buttons to allow the user to initiate and terminate calibration. In other embodiments, the user interface may comprise voice or touch activation, a biased switch, etc. Additionally, the user interface may be another device, such as a handheld device, configured to interact with the hearing protection device. The processor may be located within the hearing protection device and may interact with (e.g. be electrically coupled to) the speaker. Typically, hearing protection device embodiments would have two modes: a calibration mode and a normal operating mode. In calibration mode, the processor may be configured to run a calibration test (by interacting with the speaker), thereby generating an individualized threshold, which may be applied in normal mode to limit the input signal. Then, the speaker in normal mode may generate a sound based on a signal received from the processor with regards to the input signal. In some embodiments, there may be an amplifier located within the hearing protection device configured to control the test sound volume/amplitude level at the speaker by controlling the test sound level signal. In this manner, the test sound volume/amplitude level (during calibration testing) would be gradually increased, by increasing the test sound level signal during the calibration test.

Typically, the hearing protection device may comprise two modes: a calibration mode and a normal mode. Generally, the user interface may be configured/operable to switch between the normal mode and the calibration mode. In calibration mode, the processor would perform a calibration test (using the speaker) with input from the user (for example the user indicating when the test sound level becomes uncomfortable) via the user interface. Once a calibration test has been performed, normal mode would typically comprise the processor capping the input signal (for example the processor reducing the input signal downward if it is higher than what the user indicated is uncomfortable). In other words, calibration testing would generally only be run if/when the user prompts the system to initiate calibration mode (although in some embodiments, calibration testing might automatically occur on start-up). In other instances, the system default would typically be to run in normal mode. During normal mode, in the case that the calibration test has been run and the user has completed the test to determine his/her own individualized threshold (in other words, the maximum test sound level the user indicated was comfortable), the processor would cap the input signal at the individualized threshold level. However, in the case that the calibration test has not been run and/or the user opted to not complete the calibration test, the processor would cap the input signal at a standard threshold level (e.g. 82 dBA).

In an embodiment, for calibration mode, the user may initiate the calibration test by using the user interface to place the hearing protection device in calibration mode. During calibration mode, the speaker may be configured to generate a test sound towards a user's ear canal based on a test sound signal from the processor (e.g. convert the test sound signal (from the processor) into a test sound). Initially, the test sound may be set to a minimum test sound volume/amplitude level by setting the test sound level to a minimum level with the volume/amplitude of the sound being increased as the calibration test proceeds (until the user indicates discomfort or the sound reaches the standard threshold). Typically, the test sound might be configured to be at one frequency, and for example might be a single frequency (e.g. a pure tone at 1, 2, or 4 kHz). Thus, the processor would generally increase the test sound volume/amplitude level at one frequency during calibration testing. Keeping the test sound level at one frequency may decrease the time it would take to complete the calibration test. Additionally, it may make it easier for the user to determine his/her individualized threshold level. However, the test sound level may be configured by the processor to occur across multiple frequencies. This may increase the calibration test time, but increase the processor's ability to accurately cap input signals across multiple frequencies. The processor may increase (e.g. incrementally) the test sound level by generating and transmitting to the speaker a test sound level signal which increases the volume/amplitude of the test sound over the previous test sound level. Generally, the processor would keep increasing the test sound level until the user deactivates the calibration test (for example when the user determines the test sound level is uncomfortable) via the user interface causing a termination signal to be sent to the processor. However, in some embodiments, the processor may stop increasing the test sound level if the user has not deactivated the calibration test and the test sound level has reached the standard threshold (e.g. 82 dBA). Once calibration testing has been terminated, the processor stores the maximum/last test sound level as the individualized threshold. The individualized threshold may serve as a cap, such that, in normal mode (with sounds having volume/amplitude greater than the cap being reduced down to the cap threshold), no volume/amplitude greater than this cap would be transmitted into the user's ear canal.

In an embodiment, once calibration mode has been deactivated, the processor may be configured to enter normal mode. Typically, during normal mode, the processor may be configured to cap the input signal based on the individualized threshold stored during the calibration test (in the event a calibration test has been run), or the processor may be configured to cap the input signal at a standard threshold (e.g. 82 dBA) in the case no calibration test has been run. In the case calibration has been run, the processor may compare the input signal volume/amplitude to the individualized threshold stored within the processor. For any input signal volume/amplitude greater than the individualized threshold, the processor may reduce the input signal volume/amplitude downward to the individualized threshold as the pass-through signal. On the other hand, for any input signal volume/amplitude lesser than or equal to the individualized threshold, the processor may pass through the input signal volume/amplitude as unchanged. In the case no calibration test has been run (such that there is no individualized threshold), the processor may compare the input signal volume/amplitude to the standard threshold (e.g. 82 dBA). For any input signal volume/amplitude greater than the standard threshold, the processor may reduce the input signal volume/amplitude downward to the standard threshold as the pass-through signal. On the other hand, for any input signal volume/amplitude lesser than or equal to the standard threshold, the processor may pass through the input signal volume/amplitude as unchanged. Thus, in normal mode, any input signal volume/amplitude that the processor measures, compares, and accepts or changes via (software) processing and transmits to the speaker may be known as the pass-through signal. In other words, the pass-through signal would be whatever portion of the input signal the processor transmits or passes through to the speaker (which would be capped at either the individualized threshold or the standard threshold). In this manner, the sound level transmitted to the speaker via the processor is capped based on an individualized threshold or standard threshold to protect the user's heating over a period of time. While persons of skill should understand the disclosed embodiments based on the above disclosure, the following figures may provide specific examples that may further clarify the disclosure.

Turning now to the drawings, FIG. 1 illustrates a perspective view of an exemplary hearing protection device 100. The hearing protection device is depicted as an earmuff device in FIG. 1 and comprises two earcups 101, each having speakers 103 and a sealing element 102; an external microphone 107 (mounted on the exterior of the earcups); a wireless communication device 108 (such as a built-in radio communicator); a port/plug 104 (operable to allow an external entertainment device such as an iPod/mp3 or communication device or separate microphone (e.g. instead of one mounted on the hearing protection device) to provide an input signal); and a user interface 106 including one or more buttons 105. In FIG. 1, the user interface 106 is located on the exterior of the hearing protection device and may optionally comprise a screen (for example configured to show the user which mode the device is in, whether calibration mode is on or off, what the current individualized threshold is, etc.). In other embodiments, there may be a light indicator (for example configured to show the user if calibration mode is on (e.g. light is red) or if calibration mode is off (e.g. light is green)). Also, in some embodiments, the user interface 106 may comprise audio software programmed to guide the user through calibration testing. Additionally, in the exemplary embodiment shown in FIG. 1, the user interface 106 comprises one or more buttons 105 (to allow the user to initiate and/or terminate calibration mode for example). In other embodiments, the user interface 106 may comprise voice or touch activation with regards to running calibration mode. Persons of skill should appreciate the types of user interface elements which would function effectively to allow the user to initiate and terminate calibration. Customarily, to activate calibration mode, the user may press and hold the one or more buttons 105, and to deactivate calibration mode, the user may release/depress the one or more buttons 105. In another embodiment, the user may press and release the button to activate the calibration mode and press and release the button a second time to deactivate the calibration mode. Additionally, in FIG. 1, the port/plug 104 configured to allow an external entertainment device to provide an input signal is an auxiliary port, but a person of skill should appreciate other types of ports/plugs 104 which would function effectively to connect an external device to the heating protection device to transmit an input signal.

Figure 2:
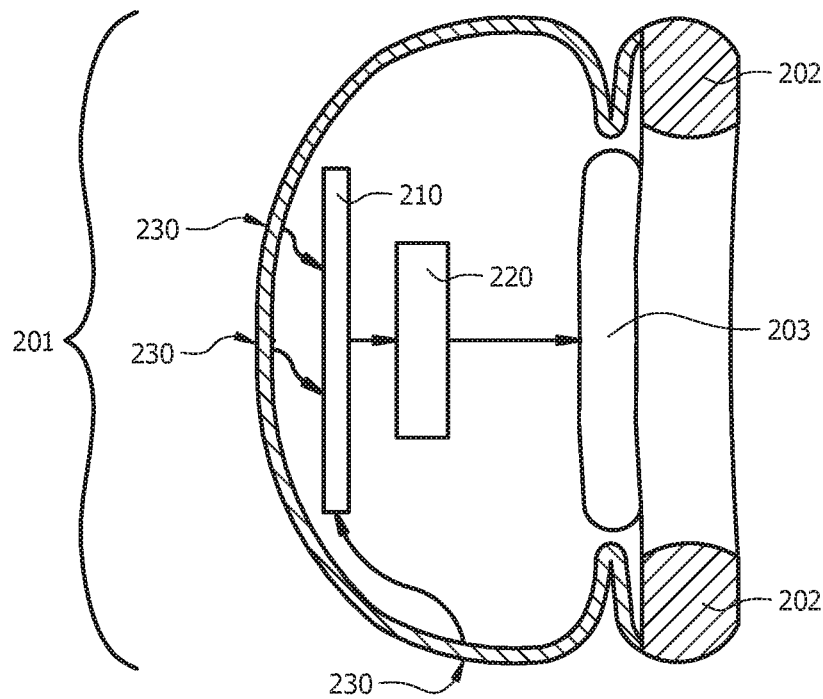
FIG. 2 illustrates a cross-sectional view of an exemplary embodiment of an earmuff hearing protection device comprising a processor, amplifier, speaker, and a sealing element.

FIG. 2 illustrates a cross-sectional view of an exemplary earcup 201 embodiment of an earmuff hearing protection device comprising a processor 210, amplifier 220, speaker 203, and a sealing element 202. The processor 210 in the embodiment of FIG. 2 is a microcontroller unit (MCU) 210 which communicates with the amplifier 220, which then communicates with the speaker 203 to transmit sound to the user's ear canal. The MCU 210 further comprises memory which may comprise electrically erasable programmable read-only memory (EEPROM). During calibration mode, the MCU 210 may communicate with the amplifier 220 to increase (e.g. incrementally) the test sound volume/amplitude level signal from a minimum test sound volume/amplitude level signal to a maximum test sound volume/amplitude level signal. Also during calibration mode, the amplifier 220 may communicate to the speaker 203 to convert the test sound volume/amplitude level signal into a sound generated into a user's ear canal (at the corresponding volume/amplitude). During normal mode, the MCU 210 may communicate with the amplifier 220 to cap (e.g. decrease) the input signal 230 (or any portion thereof in excess of the threshold) to either the individualized threshold (in the case that the calibration test has been completed) or the standard threshold (in the case that no calibration test has been completed). The input signal 230 which is passed through the amplifier 220 (and capped via the MCU 210) may then be a pass-through signal which may be transmitted to the speaker 203 to generate a sound. Additionally, in FIG. 2, the sealing element 202 configured to cover around the perimeter of the user's ear provides further protection against an external noise environment and reduces/attenuates the external noise/sound entering the user's ear canal. For example, the sealing element 202 may provide a Noise Reduction Rating (NRR) of 20-32, 20-30, 20-25, 22-25, 22-30, or 25-30, by way of example.

Figure 3:
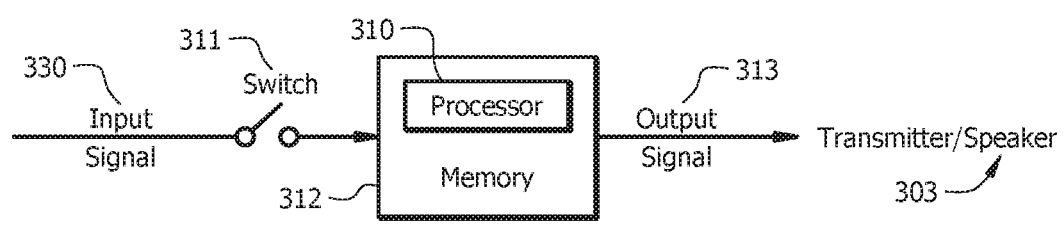
FIG. 3 illustrates an overall diagram of an exemplary embodiment of a system used to calibrate an input signal using a processor (and transmit a sound through a speaker)

FIG. 3 illustrates an overall diagram of an embodiment of a system (typically used within a hearing protection device) used to calibrate an input signal 330 using a processor 310. The input signal 330 may be from an input signal source which may be an external microphone, a wireless communication device, or an external device such as an iPod/mp3 (for example, via a port/plug in the hearing protection device) to provide an input signal 330 to the processor 310. In FIG. 3, the processor 310 may be configured to access its memory 312 to determine the user configured parameters and to execute software processing. In some embodiments, the memory 312 may be an EEPROM, but in other embodiments, the memory 312 may be in the form of RAM. Persons of skill should appreciate the types of memory 312 technologies which would function effectively to store information being processed by a processor (for example, a MCU). FIG. 3 further comprises a switch 311 (which might typically interact with or be a part of the user interface). In the embodiment of FIG. 3, the switch 311 may be opened when the user prompts the user interface to begin calibration node. Upon termination of the calibration mode, the switch 311 may be closed to indicate to the processor 310 to run in normal mode. In some embodiments, in normal mode, the processor 310 may execute software processing to reduce any input signals 330 greater than the individualized threshold (in the case that the calibration test has been completed) or the standard threshold (in the case that the calibration test has not been initiated or completed) and allow all other signals at or below the corresponding threshold to pass-through as an output signal 313. The output signal 313 may then be transmitted via a transmitter/speaker 303 to the user's ears as sound.

Figure 4:
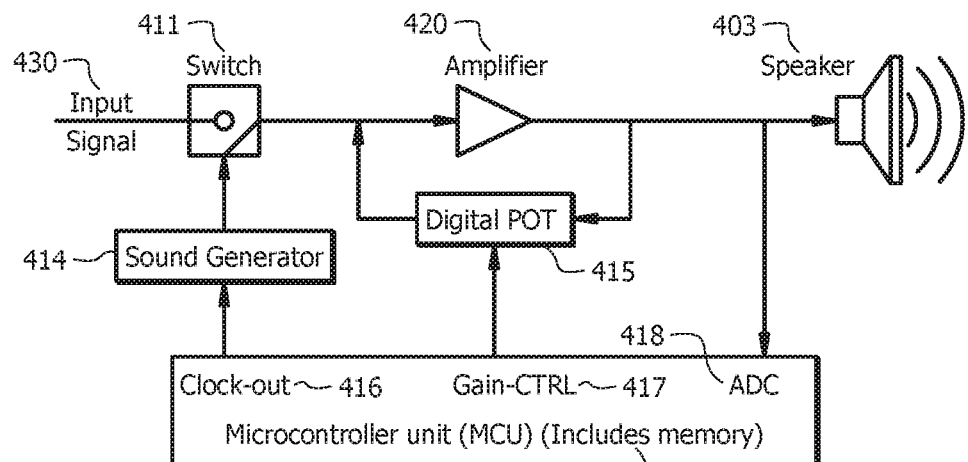
FIG. 4 illustrates, via a detailed diagram, an exemplary embodiment of a system used to calibrate an input signal using a processor (and transmit a sound through a speaker)

FIG. 4 illustrates a more detailed diagram of an embodiment of a system used to calibrate an input signal 430 comprising a switch 411, an amplifier 420, a sound generator 414, a digital potentiometer (POT) 415, a processor 410 (shown as MCU in FIG. 4), memory, and a speaker 403. During calibration mode, the user may initiate calibration testing via the user interface. Upon initiation of calibration testing, the switch 411 located directly after the input signal 430 may be opened to connect with the sound generator 414 (e.g. so the input signal 430 is not electrically connected to the speaker 403). When this occurs, the processor 410, which further comprises a clock generator 416 (shown as clock-out in FIG. 4) in this embodiment, may then be configured to produce a (digital) timing signal to the sound generator 414. Then the processor 410 may instruct the sound generator 414 to generate a standard tone (e.g. 1, 2, or 4 kHz) (or alternatively generate a sound across multiple frequencies). This would generally be accomplished by the sound generator 414 which may be configured to transform the (digital) timing signal (from the clock generator 416) into the test signal (which is an analog signal). Upon determination from the user interface that the test sound level is acceptable (e.g. not too loud so as to be uncomfortable to the user), in the embodiment of FIG. 4 the processor 410 may implement its auto gain controller (AGC) 417 (shown as gain-ctrl in FIG. 4) to interact with the digital POT 415, which may be configured to interface with the amplifier 420 to steadily increase the volume/amplitude of the test sound level. The processor 410 may continue increasing the test sound volume/amplitude level until the user indicates the test sound volume/amplitude level is uncomfortable (via the user interface). Additionally, the processor 410 contains an analog-to-digital converter (ADC) 418 in the embodiment shown in FIG. 4. This may be due to the fact that the processor 410 processes data only in the digital form and the test sound signal levels may only be transmitted in analog form. The ADC 418 may pull/read the maximum sound level (signal) during calibration, which may then be recorded to the memory (for example, use of the individualized threshold in normal mode).

During normal mode, the switch 411 shown in FIG. 4 would generally be closed to allow the input signal 430 to interface with the speaker 403 (and, for example, via the amplifier 420, with the processor 410). The processor 410 may then compare the input signal 430 with a standard threshold (in the case no calibration test has been run/completed) or an individualized threshold (in the case a calibration test has been run/completed). For any input signal 430 levels greater than the corresponding threshold, the processor 410 may act to cap the input signal 430 (e.g. reducing such excess volume/amplitude downward to the appropriate threshold). For example, the processor's gain-ctrl 417 may work in maximum gain by default and may follow a closed-loop feedback regulating circuit to reduce the gain to match the threshold signal level. This may be done by the gain-ctrl 417 interfacing with the digital POT 415 to transmit a reduced input signal 430 (volume/amplitude) to the amplifier 420 which may then further adjust the volume/amplitude (upon determination the input signal 430 (volume/amplitude) is greater than the corresponding threshold). The processor 410 may be able to gather input signal 430 (volume/amplitude) levels via the ADC 418 to determine if the input signal 430 (volume/amplitude) levels are acceptable (within the corresponding threshold limit). Once the processor 410 determines the input signal 430 (volume/amplitude) is less than or equal to the corresponding threshold, the processor 410 may pass the input signal 430 through as a pass-through signal. The pass-through signal may then be transmitted to the user's ear canal via the speaker 403.

Figure 5:
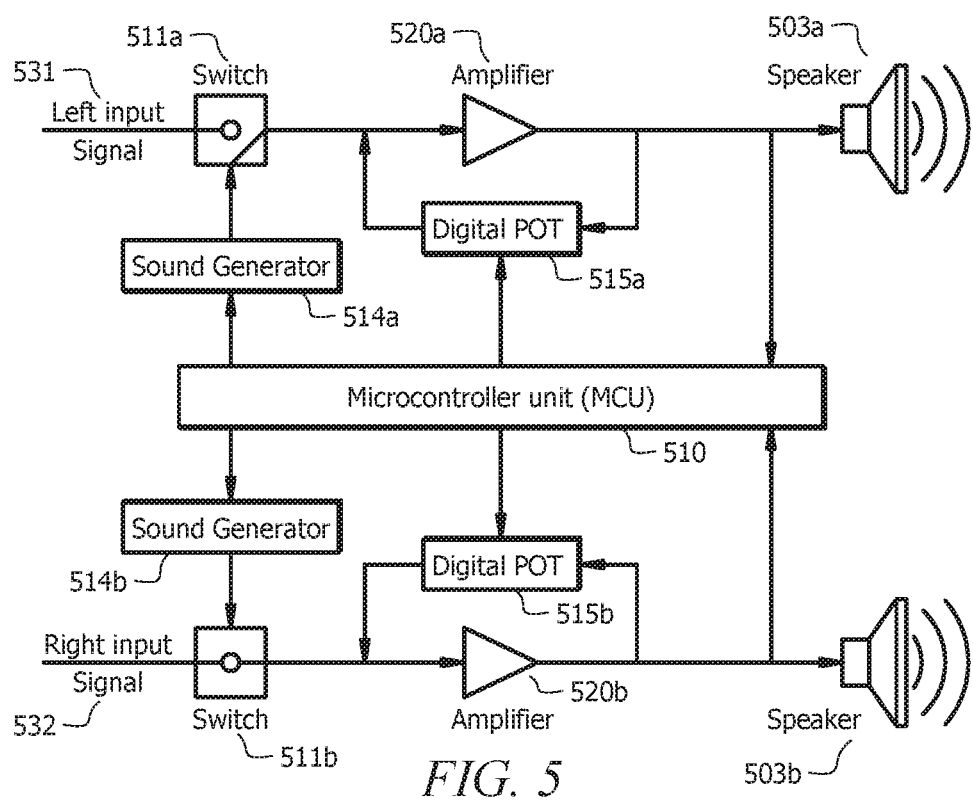
FIG. 5 illustrates, via a detailed diagram, an exemplary embodiment of a system used to calibrate a left input signal and a right input signal using a processor (e.g. for both ears of a user wearing an earmuff)

FIG. 5 illustrates a detailed diagram of an embodiment of a system used to calibrate an input signal (531, 532) similar to the detailed diagram shown in FIG. 4. The embodiment of a system shown in FIG. 5 comprises the following similar elements to the embodiment of a system shown in FIG. 4: input signal (531, 532), switch (511a, 511b), amplifier (520a, 520b), speaker (503a, 503b), digital POT (515a, 515b), sound generator (514a, 514b), microcontroller unit (MCU) (510). However, in this case, the system is configured for two ears. In other words, as shown in FIG. 5, there is a left input signal 531 (for example for the user's left ear) and a right input signal 532 (for example for the user's right ear). The user may choose to calibrate both ears at once (for example the switch (511a, 511b) after both the left input signal 531 and the right input signal 532 may be open). The user may also choose to calibrate each ear individually (for example, the switch (511a) for the left ear is open to undergo calibration testing and the switch (511b) for the right ear is closed or vice versa). In FIG. 5, the switch 511a for the left input signal 531 is open to indicate the user may have initiated calibration testing for his/her left ear, and the switch 511b for the right input signal 532 is closed to indicate the user may not have initiated calibration testing for his/her right ear (e.g. the right ear may be in normal mode).

In operation, calibration mode and normal mode for each ear in FIG. 5 would essentially perform as described above with regards to FIG. 4. In another aspect, the disclosure includes two methods: a calibration mode method and a normal mode method. The calibration mode method comprises calibrating a hearing protection device with a speaker to an individual user to determine an individualized threshold. The normal mode method comprises capping an input signal from an input signal source to the individualized threshold (in the case the calibration test has been completed) or a standard industry threshold (e.g. 82 dBA) (in the case the calibration test has not been completed). And often times, the normal mode method of operation might follow the calibration mode method of operation. The two methods are further described in the following figures which may provide specific method steps that may further clarify the disclosure.

Figure 6:
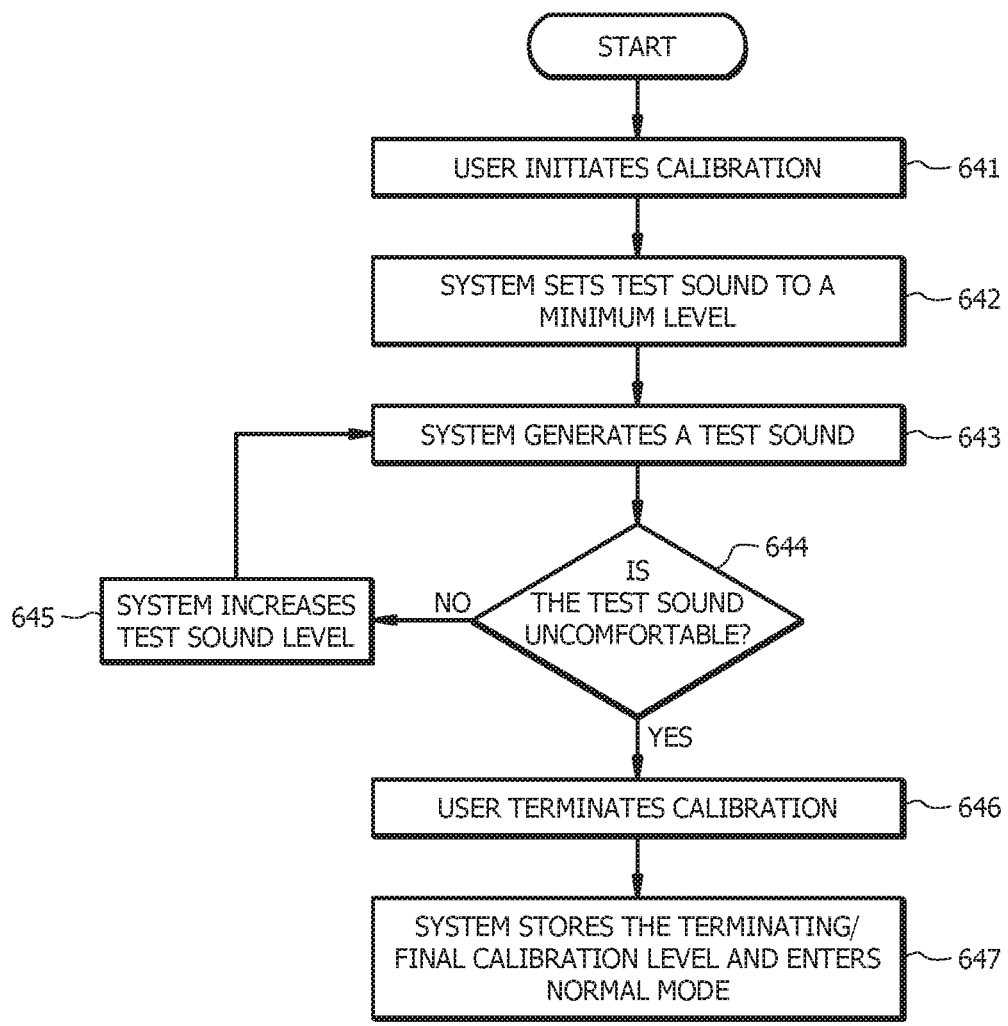
FIG. 6 illustrates, via a flowchart, a method of performing an exemplary calibration test (for example using a user interface)

FIG. 6 illustrates a flow chart of a method of performing a calibration test. To enter calibration mode, the user interacts with the user interface to initiate calibration 641. This may initiate the calibration test, by the processor, in response to an initiation signal received from the user interface. Once an initiation signal may be received, the processor generates a minimum test sound volume/amplitude level by setting the test sound to a minimum test sound level 642 (which typically would be stored in the memory). The processor then generates a minimum test sound 643 (for example by communicating with the sound generator). In the case the user determines the test sound is comfortable and does not deactivate calibration mode 644, the processor may instruct the amplifier to increase the test sound level 645 (signal) (for example in an incremental manner). Once the test sound level signal is increased 645, the processor instructs the sound generator to generate the test sound 643. This may increase in test sound level signal (and the corresponding volume of the test sound) may continue iteratively (in a loop, as shown in FIG. 6), until either the standard threshold is reached or the user deactivates calibration mode). In the case the user determines the test sound is uncomfortable 644 and terminates the calibration test 646 (which may simultaneously deactivate calibration mode), the processor stores the terminating/final calibration level (in memory) and enters normal mode 647 (for example as discussed below with regards to FIG. 7).

Figure 7:
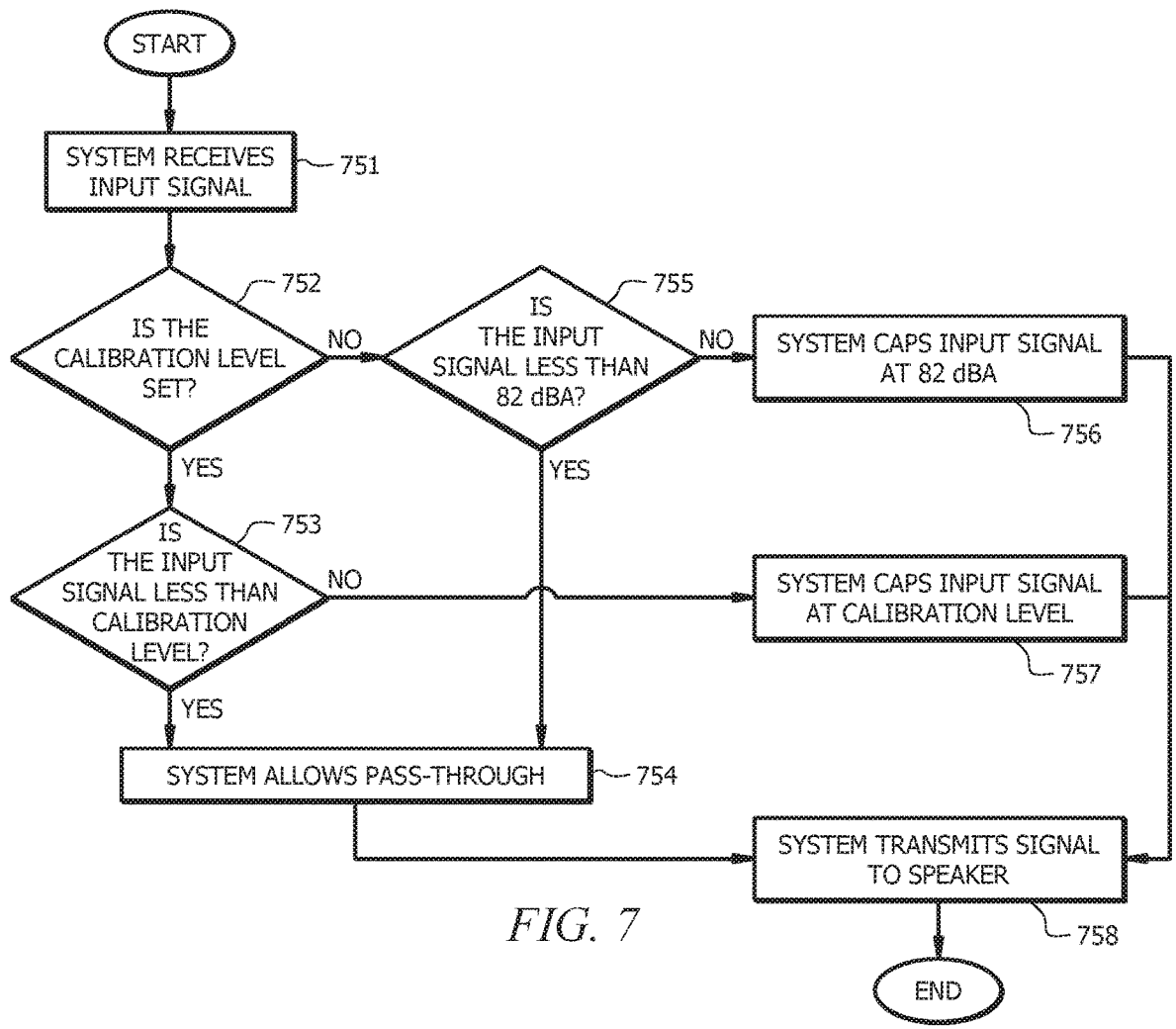
FIG. 7 illustrates, via a flowchart, an exemplary operation of a hearing protection device operable to run a calibration test to set an individualized threshold.

FIG. 7 illustrates a flow chart of a method of the hearing protection device running in normal mode (which for example, might occur after calibration or alternatively if there has been no calibration). The processor may run in normal mode at all times the hearing protection device is receiving an input signal 751 via a sound signal source and is not in calibration mode. Once the system receives an input signal 751 (e.g. from a sound signal source), the processor may use software processing to determine if a calibration level (e.g. individualized threshold) has been set 752. Upon determining a stored calibration level exists (for example within the processor's memory), the processor may compare the input signal volume/amplitude with the calibration level. For an input signal volume/amplitude greater than the calibration level 753, the processor reduces (caps) the input signal downward to the calibrated level 757 (e.g. 82 dBA in the embodiment of FIG. 7) and transmits the signal to the speaker 758. For an input signal volume/amplitude less than or equal to the calibration level 753, the processor passes through the input signal unchanged as the pass-through signal 754. Upon determining no stored calibration level exists 752 (e.g. within the processor's memory), the processor may compare the input signal volume/amplitude with the standard threshold (e.g. 82 dBA). For an input signal volume/amplitude greater than the standard threshold 755, the processor reduces the input signal downward to the standard threshold 756 and transmits the signal to the speaker 758. For an input signal volume/amplitude less than or equal to the standard threshold level 755, the processor passes through the input signal unchanged as the pass-through signal 754. For all input signals that are passed through the processor as a pass-through signal 754, the processor may transmit the pass-through signal to the speakers 758. The speakers may generate a corresponding sound into the user's ear canal.

Having described device and method embodiments above, especially with regard to the figures, various additional embodiments can include, but are not limited to:

In a first embodiment, a hearing protection device may comprise: a sealing element (operable/configured to seal a user's ear canal to protect against an external noise environment and/or reduce/attenuate external sound experienced by the user's ear canal); a speaker; a processor; a sound signal source operable to provide an input signal; and a user interface; wherein: the hearing protection device has a normal mode and a calibration mode; in calibration mode, the processor is configured to run a calibration test (by transmitting a test sound signal to the speaker) to generate an individualized threshold (e.g. cap); and in normal mode, the processor is configured to apply the individualized threshold to cap/limit the input signal (so that the speaker will not generate sound in excess of the cap/limit (e.g. the maximum test sound level from the calibration test) to generate a pass-through signal; and the speaker is configured to generate sound based on the signal received from the processor. A second embodiment can include the hearing protection device of the first embodiment, wherein in calibration mode, the speaker is configured to generate a test sound based on a test sound signal from the processor (e.g. convert the test sound signal (from the processor) into a test sound); and in normal mode, the speaker is configured to generate a pass-through sound based on the pass-through signal (e.g. convert the pass-through signal into pass-through sound). A third embodiment can include the hearing protection device of the first or second embodiments, wherein (in calibration mode) the processor is configured (e.g. by executing software processing configured) to run the calibration test comprising: generating, by the processor, a minimum test sound (volume/amplitude) level signal and transmitting the minimum test sound level signal to the speaker; (generating, by the speaker, in response to the minimum test sound (volume/amplitude) level signal, a minimum test sound); generating, by the speaker, in response to the test sound (volume/amplitude) level signal, the test sound (in the user's ear canal); (incrementally) increasing the test sound level (by the processor generating and transmitting to the speaker a test sound level signal which incrementally increases the volume/amplitude of the test sound over the previous test sound level); (continue (incrementally) increasing the test sound level); terminating the calibration test, by the processor, in response to a first of a termination signal from the user interface; or the test sound level reaching a standard threshold (e.g. 82 dBA); and storing, by the processor (in memory/storage), the maximum/last test sound level as the individualized threshold (e.g. a dBA or loudness/volume threshold) (which serves as a cap, such that no volume/amplitude greater than this cap will be transmitted into the user's ear canal). A fourth embodiment can include the hearing protection device of any of the first to third embodiments, wherein (in normal mode) the processor is configured to generate the pass-through signal (e.g. by executing software processing) comprising: comparing the input signal (volume/amplitude) to the individualized threshold; for any input signal (volume/amplitude) in excess of the individualized threshold, reducing the input signal downward to the individualized threshold (so that the speaker in response will not produce sound over the cap test sound level set during calibration) as the pass-through signal; and for any input signal (volume/amplitude) not in excess of (e.g. at or below) the individualized threshold, passing through the input signal unchanged as the pass-through signal. A fifth embodiment can include the hearing protection device of any of the first to fourth embodiments, wherein in the event no calibration test has been run, the individualized threshold is the standard threshold. A sixth embodiment can include the hearing protection device of any of the first to fifth embodiments, wherein in the event no calibration test has been run (such that there is no individualized threshold), the processor is configured to generate the pass-through signal (e.g. by executing software processing) comprising: comparing the input signal (volume/amplitude) to the standard threshold (e.g. 82 dBA); for any input signal (volume/amplitude) in excess of the standard threshold (e.g. pre-stored in memory of the processor), reducing the input signal downward to the standard threshold (so that the speaker in response will not produce sound over a standard cap sound level) as the pass-through signal; and for any input signal (volume/amplitude) not in excess of (e.g. at or below) the standard threshold, passing through the input signal unchanged as the pass-through signal. A seventh embodiment can include the hearing protection device of any of the first to sixth embodiments, wherein the user interface is operable/configured to switch between normal mode and calibration mode, and wherein in calibration mode, the user interface is operable/configured to allow a user to set the individualized threshold (e.g., by indicating when the test sound level becomes uncomfortable). An eighth embodiment can include the hearing protection device of any of the first to seventh embodiments, wherein the user interface is configured so that activation enters calibration mode and initiates calibration testing, while deactivation sets the individualized threshold and enters normal mode. A ninth embodiment can include the hearing protection device of any of the first to eighth embodiments, wherein the user interface is a button and wherein activation is pressing (and holding) the button and deactivation is releasing/depressing the button. A tenth embodiment can include the hearing protection device of any of the first to ninth embodiments, wherein the user interface is a button and activation is pressing the button and deactivation is re-pressing the button (subsequent to the initial pressing that starts the calibration test). An eleventh embodiment can include the hearing protection device of any of the first to tenth embodiments, wherein the sound signal source is one or more of: an external microphone (which might be mounted on the exterior of the hearing protection device/earcup); a wireless communication device (such as a built-in radio communicator); a (built-in) entertainment device; and a port/plug (configured/operable to allow an external entertainment device such as an iPod/mp3 to provide an input signal). A twelfth embodiment can include the hearing protection device of any of the first to eleventh embodiments, further comprising an amplifier and a digital potentiometer, wherein in normal mode, the processor interacts with the amplifier via the digital potentiometer to adjust the input signal to the pass-through signal. A thirteenth embodiment can include the hearing protection device of any of the first to twelfth embodiments, further comprising a sound generator and an amplifier, wherein in the calibration mode: the processor comprises a clock generator (e.g. clock-out); the clock generator is configured to produce a (digital) timing signal to the sound generator; the sound generator is configured to transform the (digital) timing signal (from the clock generator) into the test signal (which is an analog signal); and the processor further comprises the digital potentiometer configured to interface with the amplifier to control the test sound (volume/amplitude) level at the speaker (e.g. by controlling the test sound level signal). A fourteenth embodiment can include the hearing protection device of any of the first to thirteenth embodiments, further comprising memory storage configured/operable to store the individualized threshold from the calibration test (and the standard threshold). A fifteenth embodiment can include the hearing protection device of any of the first to fourteenth embodiments, wherein the processor is a microcontroller unit further comprising a clock generator, an auto gain controller, memory, and an analog-to-digital (ADC) converter. A sixteenth embodiment can include the hearing protection device of any of the first to fifteenth embodiments, further comprising an amplifier located between the sound signal source and the user interface. A seventeenth embodiment can include the hearing protection device of any of the first to sixteenth embodiments, wherein the clock generator produces a timing signal with which to synchronize the sound signal generated by the sound generator, and wherein the auto gain controller (AGC) is configured to reduce the input signal downward. An eighteenth embodiment can include the hearing protection device of any of the first to seventeenth embodiments, wherein the test sound is a single frequency tone (for example 1, 2, or 4 kHz) (or alternatively across multiple frequencies—e.g. multi-frequency sound/tone).

Exemplary embodiments might also relate to methods for calibrating a hearing protection device with a speaker to an individual user (e.g. similar to those described above, which may be considered optionally incorporated herein with respect to the discussion of the methods). Such method embodiments, for example, might include, but are not limited to, the following:

In a nineteenth embodiment, a method of calibrating a hearing protection device with a speaker to an individual user, comprising the steps of: performing, by a processor coupled to the speaker, a calibration test configured to determine the user's individualized threshold (for use in a normal mode to limit/cap sound generation by the speaker, for example in place of a standard threshold). A twentieth embodiment can include the method of the nineteenth embodiment, wherein performing a calibration test comprises: generating, by the processor, a minimum test sound (volume/amplitude) level signal by initially setting the test sound level to a minimum level; transmitting the minimum test sound level signal to the speaker; generating, by the speaker, in response to the test sound level signal, a test sound (in the user's ear); (incrementally) increasing the test sound level (by the processor generating and transmitting to the speaker a test sound level signal which incrementally increases the volume/amplitude of the test sound over the previous test sound level); terminating the calibration test, by the processor, in response to a first of: a termination signal from a user interface; or the test sound level reaching a standard threshold (e.g. 82 dBA), and storing, by the processor (in memory), the maximum/last test sound level as an individualized threshold (which serves as a cap, such that no volume/amplitude greater than this cap will be transmitted into the user's ear canal). A twenty-first embodiment can include the method of the nineteenth to twentieth embodiments, further comprising initiating the calibration test, by the processor, in response to an initiation signal from the user interface. A twenty-second embodiment can include the method of the nineteenth to twenty-first embodiments, wherein the hearing protection device comprises a calibration mode and a normal mode, and wherein initiating the calibration test places the hearing protection device in calibration mode, while terminating the calibration test places the hearing protection device in normal mode. A twenty-third embodiment can include the method of the nineteenth to twenty-second embodiments, wherein initiating the calibration test comprises activating (for example by depressing a button) the user interface, and terminating the calibration test comprises deactivating the user interface (e.g. button). A twenty-fourth embodiment can include the method of the nineteenth to twenty-third embodiments, wherein terminating the calibration test occurs when the user finds the test sound level uncomfortable. A twenty-fifth embodiment can include the method of the nineteenth to twenty-fourth embodiments, wherein generating a test sound (volume/amplitude) level signal comprises the processor instructing a sound generator to transmit a signal to an amplifier (and thereby to the speaker). A twenty-sixth embodiment can include the method of the nineteenth to twenty-fifth embodiments, wherein the sound generator is configured to generate a sound at one (pure tone) frequency (e.g. 1, or 4 kHz) (or alternatively across multiple frequencies). A twenty-seventh embodiment can include the method of the nineteenth to twenty-sixth embodiments, wherein the processor comprises a clock generator (e.g. clock-out), and wherein the clock generator produces a (digital) timing signal to the sound generator (which the sound generator transforms into an analog signal); and wherein the processor further comprises a digital potentiometer which interfaces with the amplifier to control the test sound (volume/amplitude) level at the speaker (e.g. by controlling the test sound level signal). A twenty-eighth embodiment can include the method of the nineteenth to twenty-seventh embodiments, wherein the processor comprises a microcontroller unit. A twenty-ninth embodiment can include the method of the nineteenth to twenty-eighth embodiments, further comprising sealing the user's ear canal (to protect the user from exposure to external noise from an external noise environment—e.g. by reducing the external sound entering the user's ear canal). A thirtieth embodiment can include the method of the nineteenth to twenty-ninth embodiments, wherein the hearing protection device comprises two earcups, each having speakers, and being operable to seal the user's ears; and wherein the method further comprises performing a calibration test for both ears. A thirty-first embodiment can include the method of the nineteenth to thirtieth embodiments, further comprising initiating the normal mode (e.g. by termination of calibration mode/terminating the calibration test); wherein in the normal mode, the processor caps an input signal (based on the individualized threshold). A thirty-second embodiment can include the method of the nineteenth to thirty-first embodiments, further comprising: receiving the input signal (by the processor); generating, by the processor, a pass-through signal (and transmitting to the speaker); and generating a pass-through sound, by the speaker, in response to the pass-through signal. A thirty-third embodiment can include the method of the nineteenth to thirty-second embodiments, wherein (in the event the calibration test has been run) generating the pass-through signal comprises: comparing the input signal (volume/amplitude) to the individualized threshold; for any input signal (volume/amplitude) in excess of the individualized threshold (e.g. stored in memory by the processor during calibration test), reducing the input signal downward to the individualized threshold (so that the speaker in response will not produce sound over the cap test sound level set during calibration) as the pass-through signal; and for any input signal (volume/amplitude) not in excess of (e.g. at or below) the individualized threshold, passing through the input signal unchanged as the pass-through signal. A thirty-fourth embodiment can include the method of the nineteenth to thirty-third embodiments, wherein generating pass-through sound, by the speaker, comprises generating sound based on the pass-through signal which is no higher (in volume/amplitude) than the individualized threshold (e.g. cap or maximum test sound level, from the calibration test). A thirty-fifth embodiment can include the method of the nineteenth to thirty-fourth embodiments, wherein, in the event no calibration test has been run (such that there is no individualized threshold), generating the pass-through signal comprises: comparing the input signal (volume/amplitude) to the standard threshold (e.g. 82 dBA); for any input signal (volume/amplitude) in excess of the standard threshold (e.g. pre-stored in memory of the processor), reducing the input signal downward to the standard threshold (so that the speaker in response will not produce sound over a standard cap sound level) as the pass-through signal; and for any input signal (volume/amplitude) not in excess of (e.g. at or below) the standard threshold, passing through the input signal unchanged as the pass-through signal. A thirty-sixth embodiment can include the method of the nineteenth to thirty-fifth embodiments, further comprising sealing (with a sealing element of the hearing protection device) the user's ear canal (to protect against an external noise environment or reduce/attenuate external noise/sound entering the user's ear canal). A thirty-seventh embodiment can include the method of the nineteenth to thirty-sixth embodiments, wherein the input signal is from one or more of: an external microphone (which might be mounted on the exterior of the hearing protection device/earcup); a wireless communication device (such as a built-in radio communicator); and an entertainment device (such as an iPod/mp3, which might be input to the hearing protection device by a sound signal source port or plug). A thirty-eighth embodiment can include the method of the nineteenth to thirty-seventh embodiments, wherein comparing the input signal (volume/amplitude) to the individualized threshold comprises comparing the input signal to the individualized threshold stored in a memory of the processor (during the calibration test). A thirty-ninth embodiment can include the method of the nineteenth to thirty-eighth embodiments, wherein generating the pass-through signal comprises the processor interacting with an amplifier via a digital potentiometer to adjust the input signal to the pass-through signal.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the inventions) set out n any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method of calibrating a hearing protection device, wherein the hearing protection device comprises two ear cups, wherein each ear cup has a sealing element, a speaker, a processor, a sound signal source, and a user interface, wherein the sealing element is configured to cover around a perimeter of the ear cup, wherein the processor and the speaker are disposed inside the ear cup and the user interface is located on an exterior of the ear cup, the method comprising the steps of:
    performing, by the processor coupled to the speaker, a calibration test configured to determine an individualized threshold of an individual user, in a calibration mode, wherein the calibration mode is initiated and terminated based on a signal received from the user interface, wherein performing the calibration test comprises:
    generating, by the processor, a minimum test sound level signal,
    transmitting the minimum test sound level signal to the speaker,
    generating, by the speaker, in response to the minimum test sound level signal, a test sound,
    increasing, by the processor, the minimum test sound level signal, in an incremental manner, in case the user determines that a test sound signal is comfortable and does not deactivate the calibration mode,
    terminating the calibration test, by the processor, in response to a first of:
        a termination signal from the user interface; or
        the test sound level reaching a standard threshold; and
    storing, by the processor, a maximum test sound level as the individualized threshold; and
    initiating a normal mode, wherein, in the normal mode, the processor is configured to cap an input signal that is higher than the individualized threshold to reduce the input signal to the individualized threshold to generate a pass-through signal.

2. The method of claim 1, wherein initiating the calibration test places the hearing protection device in the calibration mode, while terminating the calibration test places the hearing protection device in the normal mode.

3. The method of claim 2, wherein initiating the calibration test comprises activating the user interface, and wherein terminating the calibration test comprises deactivating the user interface.

4. The method of claim 2, wherein terminating the calibration test occurs when the individual user finds the test sound level uncomfortable.

5. The method of claim 1, wherein generating the minimum test sound level signal comprises the processor instructing a sound generator to transmit a signal to an amplifier, and wherein the sound generator is configured to generate a sound at one frequency.

6. The method of claim 5, wherein the processor comprises a clock generator, and wherein the clock generator produces a timing signal with which to synchronize the signal generated by the sound generator; and wherein the processor further comprises a digital potentiometer which interfaces with the amplifier to control the test sound level at the speaker.

7. The method of claim 1, further comprising:
    receiving the input signal;
    generating, by the processor, the pass-through signal; and
    generating a pass-through sound, by the speaker, in response to the pass-through signal.

8. The method of claim 7, wherein, in an event the calibration test has been run, generating the pass-through signal comprises:
    comparing the input signal to the individualized threshold; and
    for any input signal not in excess of the individualized threshold, passing through the input signal unchanged as the pass-through signal.

9. The method of claim 7, wherein, in an event no calibration test has been run, generating the pass-through signal comprises:
    comparing the input signal to the standard threshold;
    for any input signal in excess of the standard threshold, reducing the input signal downward to the standard threshold as the pass-through signal; and
    for any input signal not in excess of the standard threshold, passing through the input signal unchanged as the pass-through signal.

10. The method of claim 7, wherein the input signal is from:
    an external microphone;
    a wireless communication device; or
    an entertainment device.

11. A hearing protection device comprising:
    two ear cups, each ear cup having:
        a sealing element configured to cover around a perimeter of the ear cup;

a speaker;

a processor, wherein the processor and the speaker are disposed inside the ear cup;

a sound signal source operable to provide an input signal; and a user interface located on an exterior of the ear cup, wherein the speaker, the sound signal source and the user interface are electrically connected with the processor;

wherein:

the hearing protection device has a normal mode and a calibration mode;

in the calibration mode, the processor is configured to run a calibration test to generate an individualized threshold, wherein the calibration mode is initiated and terminated based on a signal received from the user interface, and wherein the processor is configured to:

generate a minimum test sound level signal, transmit the minimum test sound level signal to the speaker, cause the speaker to generate a test sound in response to the minimum test sound level signal, increase the minimum test sound level signal, in an incremental manner, in case a user determines that a test sound signal is comfortable and does not deactivate the calibration mode, terminate the calibration test in response to a first of:
a termination signal from the user interface; or
the test sound level reaching a standard threshold; and store a maximum test sound level as the individualized threshold; and in the normal mode, the processor is configured to apply the individualized threshold to cap the input signal that is higher than the individualized threshold to reduce the input signal to the individualized threshold to generate a pass-through signal.

12. The hearing protection device of claim 11, wherein:
in the normal mode, the speaker is configured to generate a pass-through sound based on the pass-through signal.

13. The hearing protection device of claim 12, wherein the processor is configured to generate the pass-through signal and configured to:

compare the input signal to the individualized threshold; and for any input signal not in excess of the individualized threshold, pass through the input signal unchanged as the pass-through signal.

14. The hearing protection device of claim 13, wherein in an event no calibration test has been run, the processor is configured to generate the pass-through signal and configured to:

compare the input signal to the standard threshold;

for any input signal in excess of the standard threshold, reduce the input signal downward to the standard threshold as the pass-through signal; and for any input signal not in excess of the standard threshold, pass through the input signal unchanged as the pass-through signal.

15. The hearing protection device of claim 11, wherein the user interface is operable to switch between the normal mode and the calibration mode, and wherein in the calibration mode, the user interface is operable to allow a user to set the individualized threshold.

16. The hearing protection device of claim 15, wherein the user interface is configured so that activation enters the calibration mode and initiates calibration testing, while deactivation sets the individualized threshold and enters the normal mode.

17. The hearing protection device of claim 11, wherein the sound signal source comprises:

an external microphone;
a wireless communication device;
an entertainment device; or
a port or plug.

* * * * *